Figure 1:
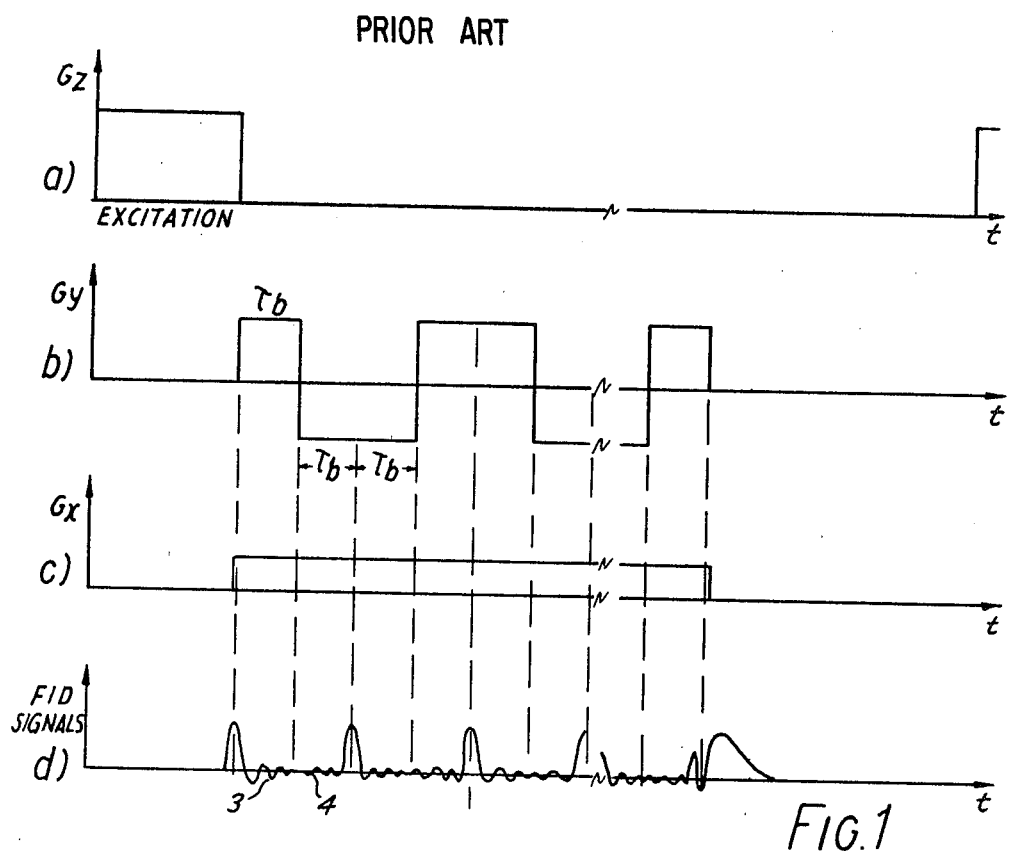

United States Patent [19]
Young et al.

[11] 4,355,282
[45] Oct. 19, 1982

[54] NUCLEAR MAGNETIC RESONANCE SYSTEMS

[75] Inventors: Ian R. Young, Sunbury-on-Thames; Michael Burl, Iver, both of England

[73] Assignee: Picker International Limited, Wembley, England

[21] Appl. No.: 173,434

[22] Filed: Jul. 29, 1980

[30] Foreign Application Priority Data

Aug. 3, 1979 [GB] United Kingdom ............... 7927119

[51] Int. Cl.³ .............................................. G01N 27/00
[52] U.S. Cl. .................................................. 324/309
[58] Field of Search ........................ 324/300, 307, 309

[56] References Cited

U.S. PATENT DOCUMENTS 4,115,730 9/1978 Mansfield ........................... 324/309
4,290,019 9/1981 Hutchison ........................... 324/309

Primary Examiner—Michael J. Tokar
Attorney, Agent, or Firm—Fleit & Jacobson

[57] ABSTRACT

The invention is related to the so-called "echo-planar" method of NMR imaging. In that method a resonance is first excited in a slice and then two orthogonal gradients provided dispersion in the slice. One gradient is pulsed to space the frequencies of spins in adjacent strips allowing the other gradient to provide dispersion down the strips. It is now proposed to pulse the second gradient so that the dephasing down each strip is also in steps. The FID signals (including rephasing signals) for each distinct element so produced can then be put in an array and two-dimensionally Fourier transformed to yield the desired output for each element.

19 Claims, 17 Drawing Figures

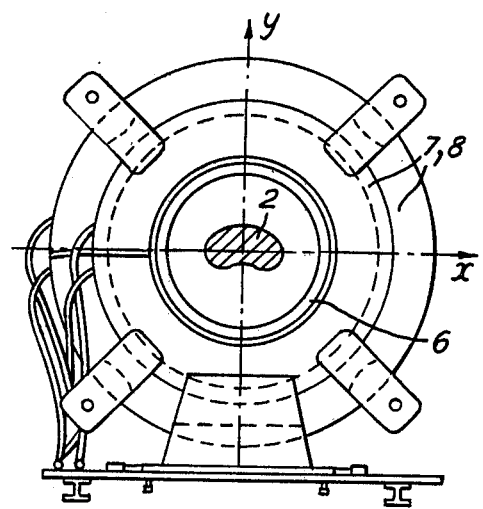
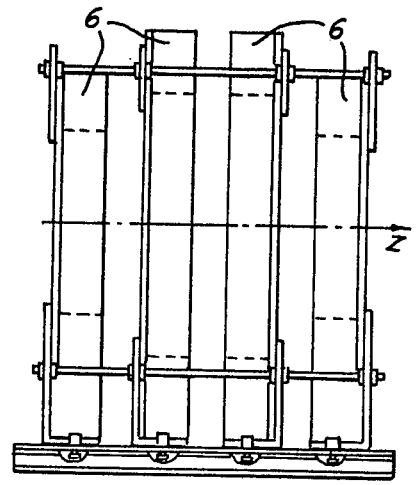
FIG.10a  FIG.10b
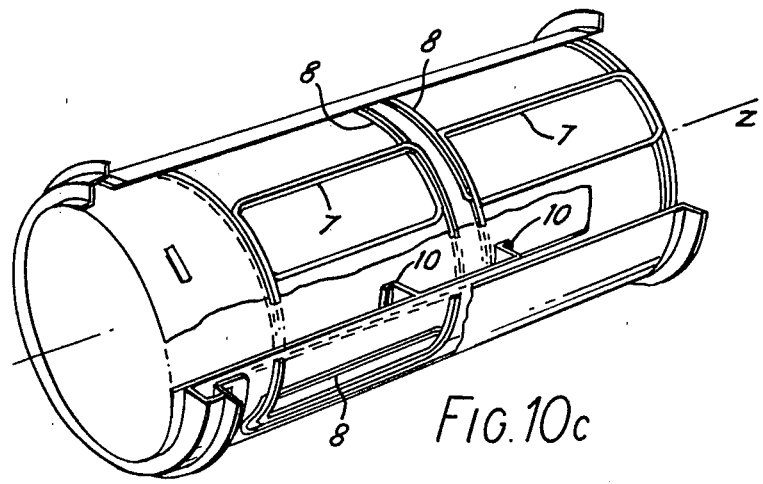
FIG.10c

NUCLEAR MAGNETIC RESONANCE SYSTEMS

The present invention relates to systems for providing, by nuclear magnetic resonance, images of distributions of a chosen quantity in a selected region of a body. The examination may be of many different kinds of bodies but a particularly beneficial application, to which much attention has been given, is the medical examination of patients.

Nuclear magnetic resonance (NMR) is now well known for the analysis of materials by spectroscopy. For medical examination it has been proposed to use variations of the technique to provide distributions of, for example, water content or relaxation time constants in sectional slices or volumes of patients. Such distributions are similar to the distributions of X-rays provided by computerised tomographic systems, although they have different significance.

For NMR examination, suitable combinations of magnetic fields are applied to the body to be examined by appropriate magnet (coil) systems. Excited material is then detected by currents induced in one or more detector coil systems and are analysed to provide the required distribution.

Various schemes have been proposed for this purpose, two which are relevant to this invention being that proposed by Mansfield and Pykett in J. Mag. Res. 29, 355-373 (1978) and that invented by Ernst and described in U.S. Pat. No. 4,070,611 and also in the paper by Kumar, Welti and Ernst in J. Mag. Res. 18, 69-83 (1975).

It is an object of this invention to provide an alternative form of such methods, and apparatus for applying that alternative method.

According to the invention there is provided a method of examining a slice of a body by nuclear magnetic resonance, the method including the steps of: applying magnetic fields to cause resonance preferentially in said slice; applying a pulsed magnetic field having a gradient across the slice in a first direction to produce phase dispersion in said resonance in said direction in the slice, the direction of the field being periodically reversed; applying a second pulsed magnetic field having a gradient across the slice in a second direction orthogonal to the first to produce a further phase dispersion in the second direction, the timing and magnitude of these field gradients being such that the slice is effectively divided into a matrix of elements, the nuclei within each of a plurality of parallel strips orthogonal to the direction of the gradient of the first pulsed field resonating within a unique frequency band and nuclei at different positions along each strip being distinguishable by phase dispersion caused by the second pulsed field; sensing free induction decay and rephasing signals emitted by the nuclei as the field gradient pulses are applied; reversing the rephasing signals to form in effect further free induction decay signals; arranging the first and further free induction decay signals in a two dimensional array to give free induction decays in the two orthogonal directions; and subjecting the signals of the array to a two dimensional Fourier Transform process.

Figure 2:
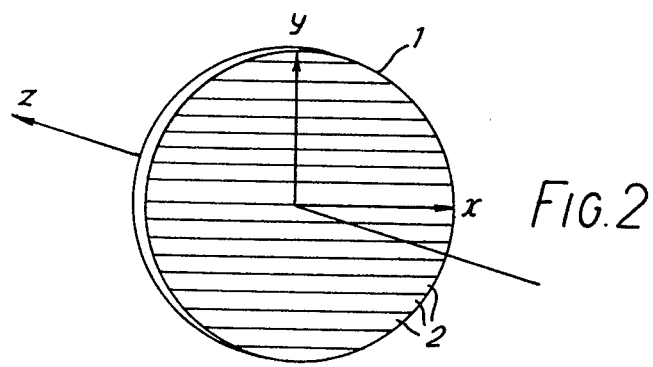
Figure 3:
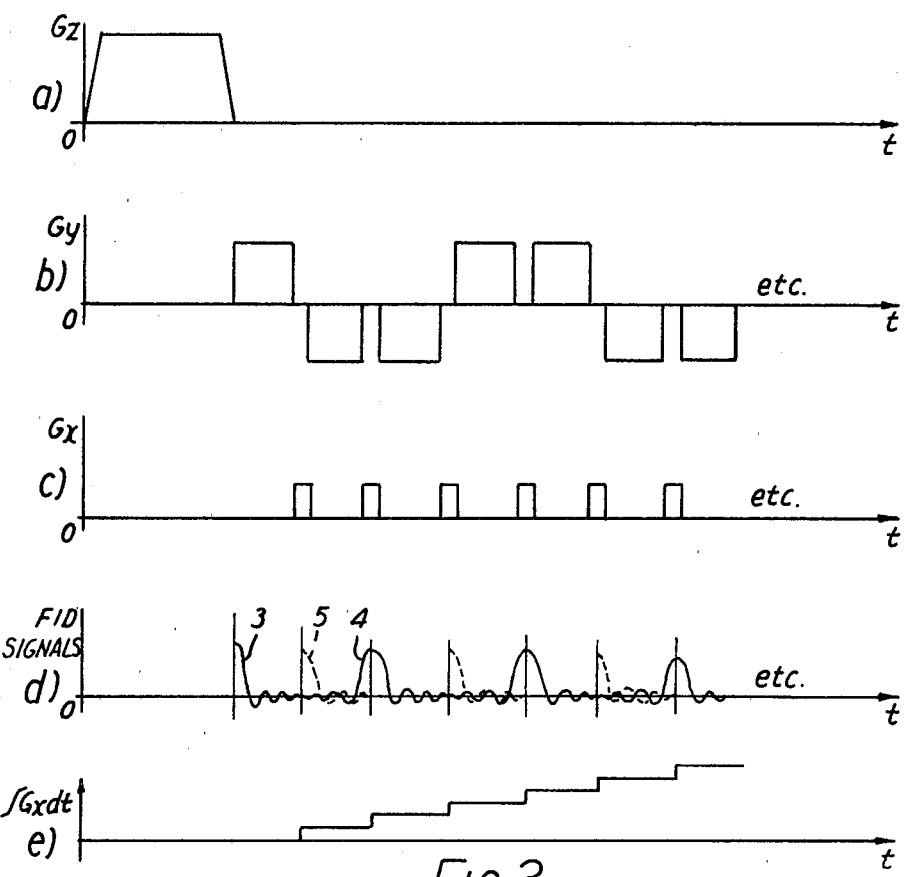
Figure 4:
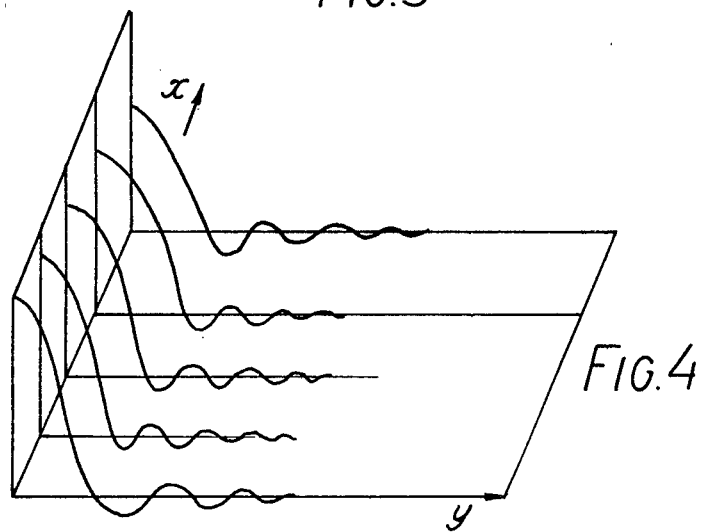
Figure 5A:
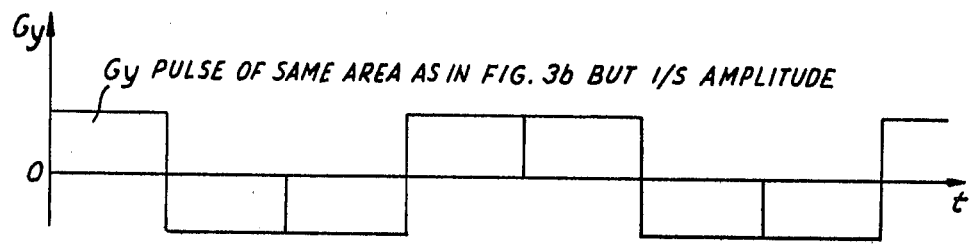
Figure 5B:
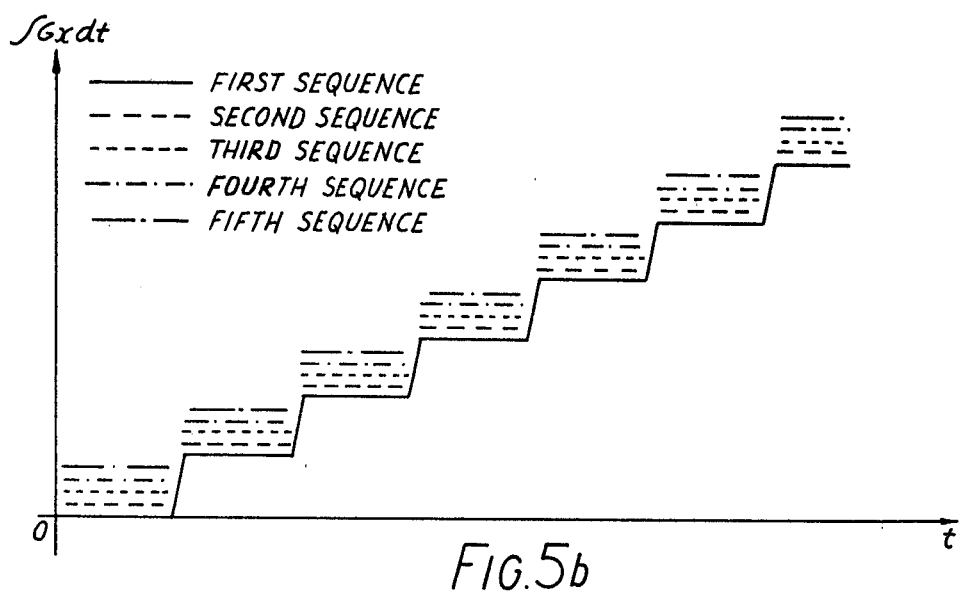
Figure 5C:
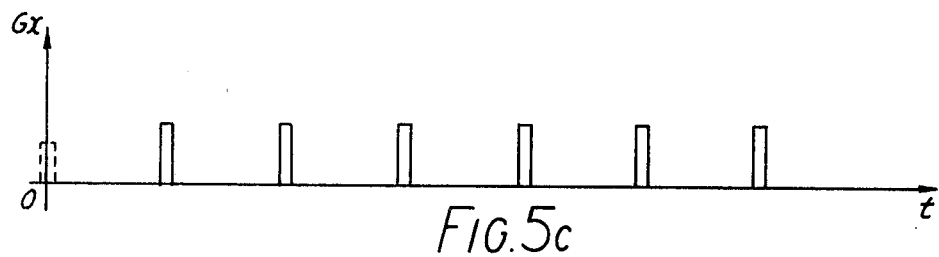
Figure 6:
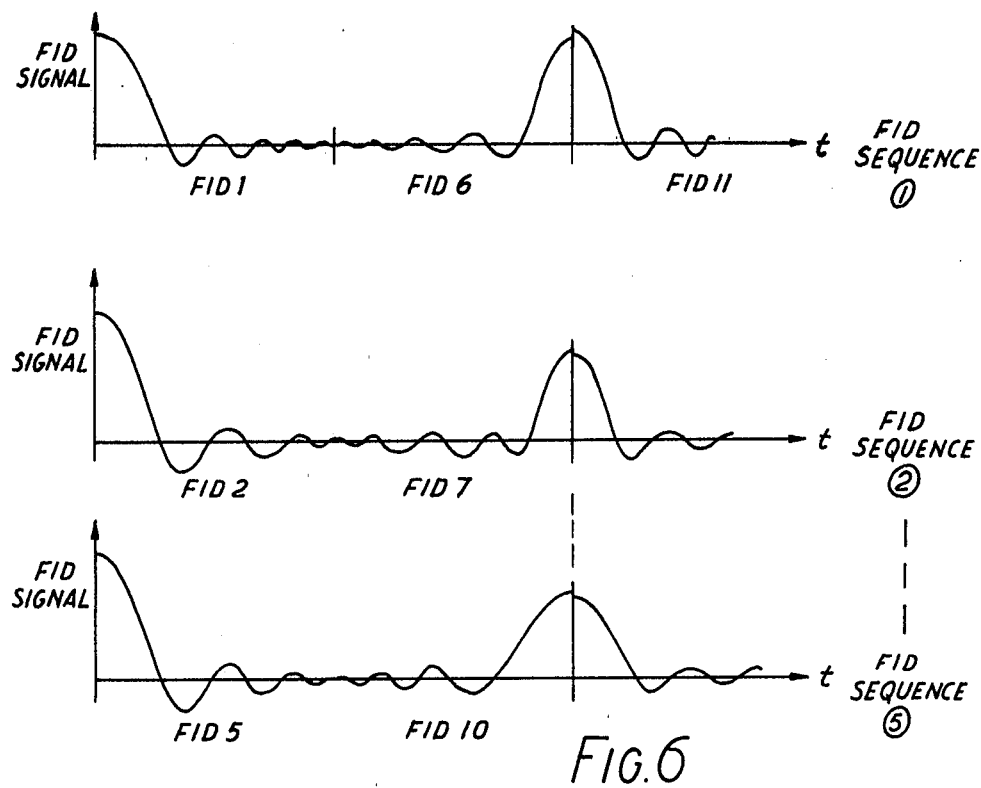
Figure 7:
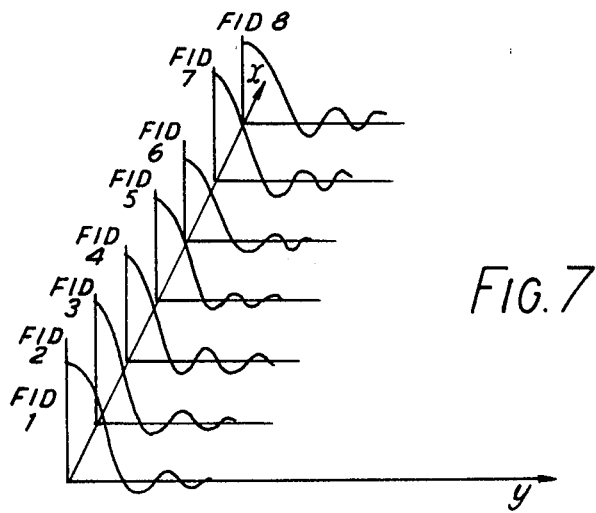
Figure 8:
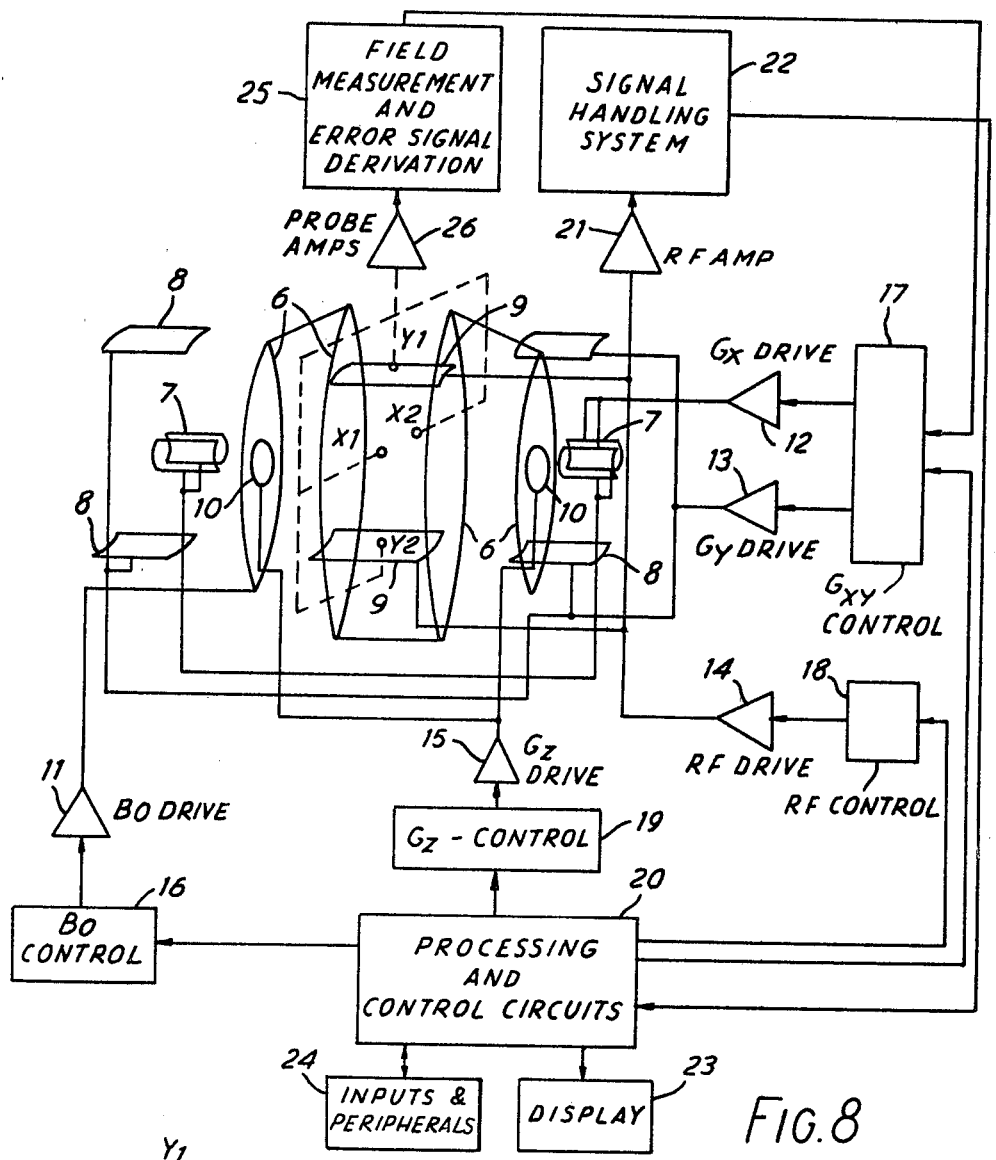
Figure 9:
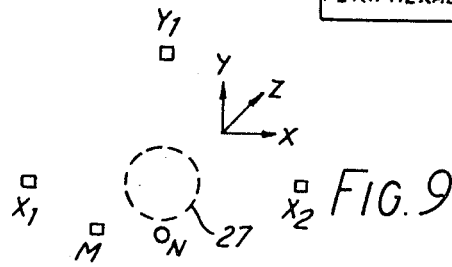
Figure 11:
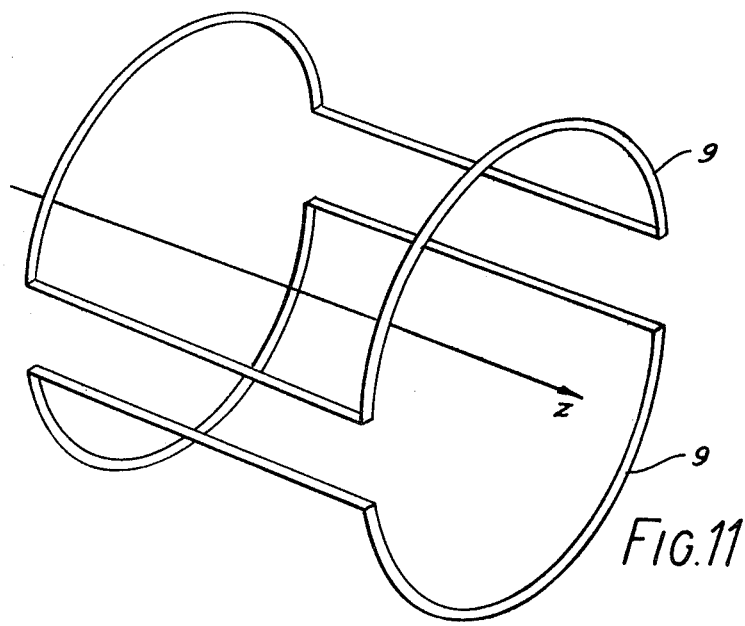
Figure 12:
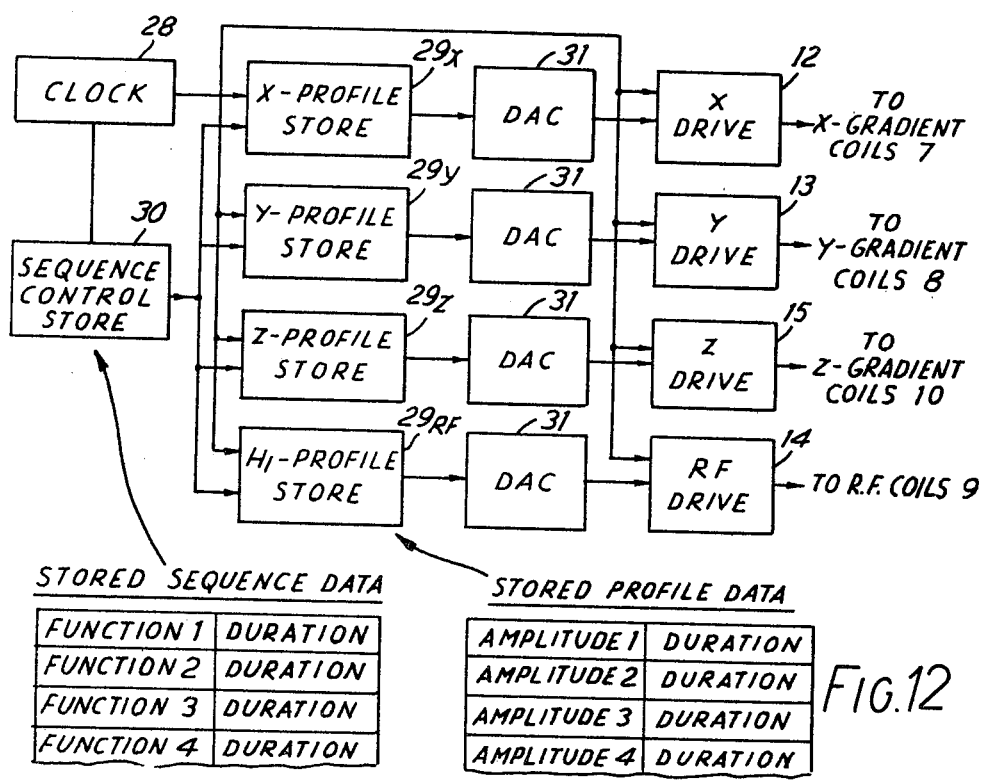
Figure 13:
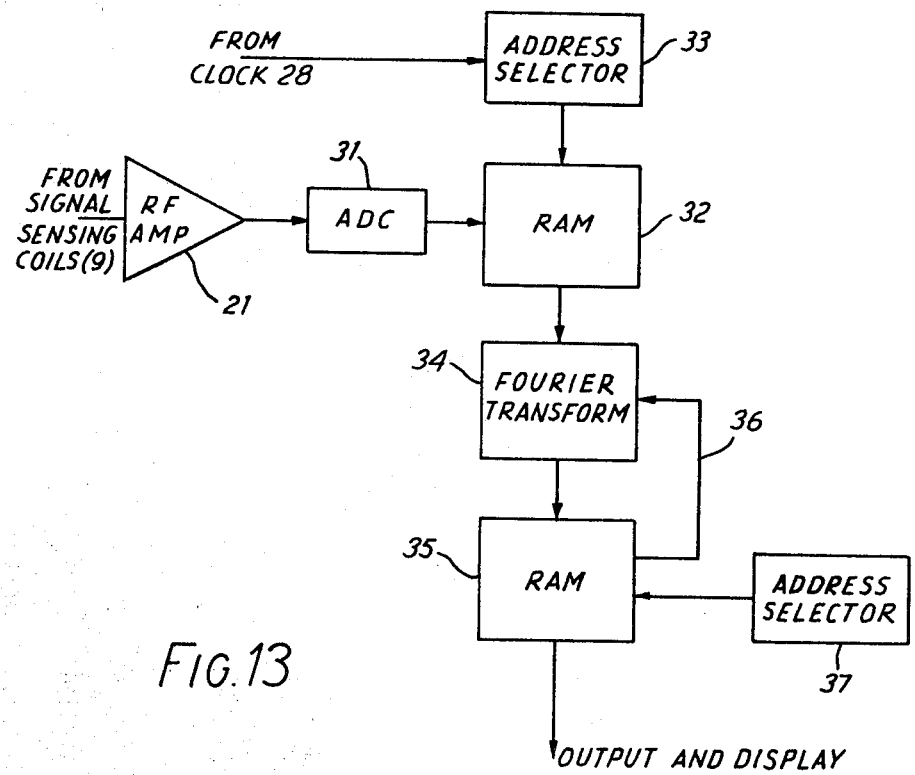

In order that the invention may be clearly understood and readily carried into effect it will now be described by way of example with reference to the accompanying drawings, of which, FIG. 1 shows the pulse sequence of and FID signals provided by a prior art method, FIG. 2 shows a body slice illustrating the effect of the sequence of FIG. 1, FIG. 3 shows the pulse sequence and FID signals provided by the method of this invention, FIG. 4 shows the manner of rearranging the FID signals in an array, FIGS. 5a, 5b and 5c show Gy pulses, Gx pulse field integrals and Gx pulses for a modification of this invention, FIG. 6 shows the FID signals resulting from the modification of FIG. 5, FIG. 7 shows how the FID signals of FIG. 7 are rearranged in an array, FIG. 8 shows schematically an apparatus which can implement this invention, FIG. 9 shows an arrangement of field measuring probes for the apparatus of FIG. 8, FIG. 10a, 10b and 10c show in end and side elevations and perspective, some of the field coils of the apparatus of FIG. 8, FIG. 11 shows RF field coils for the apparatus of FIG. 8, FIG. 12 shows in block diagrammatic form circuits for controlling the field pulses of this invention and, FIG. 13 shows in block diagrammatic form a signal handling system for the apparatus of FIG. 8, to implement this invention.

The NMR procedure proposed by Mansfield and Pykett is known as "Echo-planar imaging" and, in common with many other techniques, involves exciting resonance in a region of the body, usually a cross-sectional slice, and causing a frequency dispersion in the slice so that resonance signals received at a particular frequency relate to a more limited regions only. In the echo-planar imaging system the more limited regions are small elements of the slice and obtaining individual resonance values for a matrix of such elements provides the required distribution.

For better understanding of the present invention it will be useful to consider the "Echo-planar" technique in more detail. The first step to be followed is to create a large uniform and steady magnetic field, which Mansfield and Pykett identify as Bo, to define the equilibrium spin polarisation axis in a direction given by a coordinate z. (Coordinates used in this description, and shown in FIG. 2, are those which will later be used in the description of the present invention and are not the same as those used by Mansfield and Pykett.) A linear magnetic field gradient $G_z = \delta B_z/\delta z$ is also applied.

Simultaneously there is applied a 90° R.F. pulse which, in well known manner, excites the spins within a region of the body for which the frequency of the R.F. pulse is substantially the Larmor frequency, as defined by the resultant magnetic field of $B_o + G_z$. FIG. 1a shows this excitation phase of the sequence. The region selected, a cross-sectional slice in this case, is shown in FIG. 2.

When the excitation phase ceases a free induction decay (FID) is produced and may be detected. During the FID a switched field gradient $Gy = \delta B_z/\delta y$ and a steady field gradient $Gx = \delta B_z/\delta x$ are both applied. The amplitude and and duration of these additional field gradients are shown in FIG. 1b and 1c respectively. It should be noted that FIGS. 1b and 1c are two different scales, the amplitudes being actually in a ratio of about 100:1.

Considering the Gy gradient, it is known that application of a steady gradient in a direction such as y (i.e. in the selected slice) causes a dispersion of the spin frequencies of the excited nuclei in that direction. Such a dispersion selects strips (2) in the slice, each strip having spin frequencies in a small range about a mean value for that strip. This detection of signals at the mean value for a strip, and within a suitably limited band, will give an FID signal for the respective strip only. The Gy pulse has a continuous spectrum Fourier transform and in practice the full FID spectrum, for the slice, is detected and is Fourier transformed to give the amplitudes at respective frequencies.

Mansfield and Pykett, however, apply a pulsed and not a steady Gy field gradient. This creates a spin echo FID signal FIG. 1d which, instead of a continuous spectrum, becomes a line spectrum of a Fourier series (because of its repetitive nature). The effect of this is that the spins of adjacent selected strips are not now at adjacent frequencies but are spaced in frequency.

The Gx field gradient is steady in the manner described above and produces a frequency dispersion in the x direction, i.e. along each slice. If, however, the value of Gx is kept small then it is possible even with the x-dispersion to avoid frequency overlap between adjacent strips. Each frequency then is unique to an elemental region of one strip and does not occur in other strips. An FID signal component at that frequency is assumed to relate only to that strip. Mansfield and Pykett then propose that the FID signals be analysed to yield the required information by being subjected to one dimensional Fourier Transform.

As thus far described the method of Mansfield and Pykett is explained in greater detail in their paper.

In considering the effect achieved by this method it will be seen that the Gy gradient can be considered to be in small steps of duration $\tau b$ and that each one of these time intervals gives an FID signal (3) or a rephasing signal (4) which is the mirror image of an FID. Although the Gy gradient causes variations with time as dephasing occurs, it will be apparent that the FID signals are continuous and, for example, the FID and rephasing signals meet at their peaks.

It is now proposed to pulse the Gx gradient so that the dephasing along the strips is also in steps rather than being continuous. The Gz, Gy and Gx gradients for this invention are thus as shown in FIGS. 3a, 3b and 3c respectively. As a result the FID signals are not continuous and each FID and each rephasing signal is slightly different from the next one even at the peaks.

As shown in FIG. 3 the Gy gradient is returned to zero amplitude during each Gx gradient pulse. This is not strictly necessary but may be advantageous.

If each rephasing signal is mirror imaged to take the same form as the FID's (broken lines 5), they can be placed in an array such as is shown in FIG. 4. This array comprises information for both the x and y dispersions and can be Fourier Transformed in two dimensions (x and y) to give the FID signals for elements in the slice. Reversal of the rephasing signals is a relatively straightforward operation since each FID or rephasing signal is usually digitised and stored in digital form before Fourier transformation. It is merely necessary to withdraw the rephasing signal from storage in the reverse order to the FID signals.

It may be observed that the action of arranging the FID signals as shown in FIG. 4 has produced signals similar to those provided by the method of Kumar, Welti and Ernst and U.S. Pat. No. 4,070,611, referenced hereinbefore, and the same method of 2-dimensional Fourier Transform described in that Patent is used to analyse them. It is emphasied however that the method of getting the signals into that form is different from and is considered to be advantageous over that described in the said Patent.

As so far described the method of this invention requires at least sixty four reversals of the large Gy gradient in typically fifty milliseconds to give sufficient dephasing in the time $\tau b$ if 128 independent variables are to be extracted. This is a typically useful figure allowing a $128 \times 128$ matrix to be evaluated for the slice.

The effect caused by the Gx field gradient is, as is now well understood for similar gradients, the effect of its field integral on the phase of the signal across the plane. If Gx is pulsed as a function of time, as suggested hereinbefore, this field integral is a staircase as shown in FIG. 3e. (In the event of a steady Gx this would be a line of constant slope). In a further aspect of this invention it is proposed that the information required for a complete evaluation of the slice is not obtained in one FID sequence such as FIG. 3d but over a larger number of such sequences. A suitable number might be five sequences and that figure will be assumed for the purposes of further description, though 8 or more could be used on occasion.

If five FID sequences are to be used, in general each Gx field integral step will be five times larger and longer. However each sequence must be different to give in combination the effect of the steps of FIG. 3e and so a variable height Gx prepulse is applied before each successive Gx sequence to cause the first field integral step to be is different in each sequence. The prepulse is zero for the first sequence and is increased by one unit for each succeeding sequence.

The five Gx integral sequences are shown in FIG. 5b for a Gy sequence as in FIG. 5a. FIG. 5 is not to the same scale as FIG. 3 and the time scale zero is set at the start of the Gy pulse sequence. The result of adopting this procedure with Gx is that the amplitude of Gy is reduced, in this example to one fifth, and the duration of $\tau b$ is increased (five times) thus reducing problems in switching the gradient. This five times procedure reduces the VI requirement for the system by a factor of twenty five. FIG. 5c shows the corresponding Gx pulse sequence with the variable height Gx pulse, set at $T=0$ for the respective sequence, being shown in broken line.

In this example of the practical system it is proposed that each 2 msec FID thus obtained is repeated twenty five times to give a measuring time of 50 msecs for one sequence and the sequence repeated (with different starting phases as described) five times to give a picture matrix of $125 \times 125$ elements. It will be apparant that rephasing should take place between each sequence and the complete pulse sequence repeated starting with the Gz pulse but with the different Gx prepulse. Rephasing can be by relaxation but is preferably forced by applying pulses negating the total Gx, Gy and Gz fields integrals in the preceding sequence, followed by a short relaxation period. Although this is a preferred procedure, the sequence can be followed straight through, with step heights as in FIG. 3e, but with each step in this example five times longer. However the sequence will still need to be broken at least five times for rephasing and will have consequent high restarting phases, which is not desirable. A further point to be noted is that although in theory a complete picture for the slice can be derived from information gained in the five sequences described, in practice this will usually need to be repeated several times in the cause of obtaining adequate signal to noise ratio.

The FID signals measured in the five sequences may be processed substantially in the manner described hereinbefore although they must be derived from storage for the Fourier Transform circuits in an interlaced order.

FIG. 6 shows the first three 'FID's' (including rephasing signals) for the first, second and fifth FID sequences, showing the order in which they must be assembled to give the array of FIG. 7 to be Fourier Transformed.

The method described hereinbefore may be performed on a suitable NMR examining apparatus such as that shown in simplified form in FIG. 8. Illustrated schematically only are coils 6, which provide the steady Bo field, 7, which provide the Gx field gradient, 8 which provide the Gy field gradient, 9, which provide the RF field and 10, which provide the Gz field gradient. The coils are driven by Bo Gx, Gy, RF and Gz drive amplifiers 11, 12, 13, 14 and 15 respectively, controlled by Bo, Gxy, RF and Gz control circuits 16, 17, 18 and 19 respectively. These circuits can take suitable forms which will be well known to those with experience of NMR equipment and other apparatus using coil induced magnetic fields. The circuits are controlled by a central processing and control unit 20 to achieve a desired pulse sequence such as that of this invention.

The FID signals sensed are received in this example by the RF coils 9 and are amplified by an RF amplifier 21 before being applied to signal handling circuits 22. In certain circumstances it may be preferable to provide separate coils specifically designed for the purpose, to sense the signal. The circuits 22 are arranged to make any appropriate calibrations and corrections but essentially transmit the signals to the processing circuits to provide the required representation of the examined slice. These circuits can conveniently be combined with the circuits which control the pulse sequence and thus are included in the circuits indicated at 20. The picture thus obtained is viewed on a display 23, such as a television monitor, and this may include inputs and other peripherals 24 for the provision of commands and instructions to the machine, or other forms of output.

The apparatus also includes field measurement and error signal circuits 25 which receive signals via amplifiers 26 from field probes $X_1$, $X_2$, $Y_1$, and $Y_2$, shown. The positions of the probes, in relation to the examined slice of the body 27 of the patient, are further shown in FIG. 10. $X_1$, $X_2$, $Y_1$ and $Y_2$ are, in this example, NMR probes which are simply miniature cells of pure water (such as a closed test tube) surrounded by a small coil. Preferably the water is doped to have a suitable value of $T_1$, relaxation time-constant. The probes give a reliable resonance of 4.26 $kHz/Oe$ and the field measured is provided by a suitable count. Other types of probe may be used as desired.

FIGS. 10a and 10b show in end and side elevation respectively a practical coil arrangement to provide the Bo field. FIG. 11a also shows the coils for production of the Gx and Gy field pulses and, to show approximate dimensions, the patient 27 in cross-section. The patient 27 is inserted in the tubular former of Gx and Gy coils 7, 8 and is supported there by a suitable couch or other supporting means. Such supports may be readily provided in any suitable form.

The coils 7, 8 are two sets of coils axially displaced, each set comprising two pairs of saddle coils the pair 7 being at 90° to the pair 8. These coils are themselves inserted into the central aperture in Bo coils 6 which are wound in four parts connected in series to provide an approximately circular configuration which is well known to be desirable for production of a uniform field.

FIG. 10c is a partially cut-away perspective view which shows the coils 7, 8 in more detail. Also visible in the cut-away are the two circular coils 10 which provide the Gz field component for the gradient superimposed on Bo.

The RF coils are shown in FIG. 11 in perspective. They are two saddle shaped coils 9 which are driven in parallel to provide the rotating RF field and which are in this example, also used to detect the FID signals which are of approximately the same frequency.

Further details of the coil winding will not be given since suitable coils can readily be devised, by those with the appropriate skills, to provide the fields required.

The operation of the four profile stores 29 is controlled by a sequence control store 30 which stores in similar manner a sequence of commands to operate the profile stores and the duration (number of clock pulses) of operation of each stage of the sequence, including gaps in the sequence. Stores 29 and 30 are conveniently programmable read only memories (PROM's).

When commanded by a central (operator) control (which is shown in FIG. 12 but which may be associated with circuits 20) the sequence control store initiates the first pulse profiles, which, as will be realised from description hereinbefore of the pulse sequence, is for RF and Gz pulses. The appropriate stores 29 provide the amplitude and duration signals which are converted to analogue form in digital to analogue convertors (DAC's) 31 and applied to respective coil drive circuits 12 (x), 13(y), 14(RF) and 15 (z). The respective drive circuits, which can take any form well known for driving field coils, provide the specified current to the appropriate coil for the specified duration.

The apparatus and circuits described so far may be adopted to provide different sequences of examining pulses, by appropriately adjusting the stored sequence and profile data. Similarly other known NMR apparatus which are capable of applying a stready magnetic field, a pulsed RF field and Gx, Gy and Gz field gradients to a body, may be adapted in a manner straightforward to those skilled in the NMR art to apply the fields described for this invention.

The basic features of the signal handling system are shown in FIG. 13. The FID signals from the signal sensing coils, in this example the RF coils 9 are amplified in an RF amplifier 21 and applied via an analogue to digital converter (ADC) 31 to a store 32, such as a random access memory (RAM).

System clock pulses from the clock 28 are also applied to the RAM 32 to indicate the timing of the pulse sequence causing the FID's and hence the identities of the FID signals. As described hereinbefore the signals are derived from RAM store 32 in a different order to that in which they are entered, and some being reversed. The reordering may be achieved on input or output from RAM store 32 as desired but is effected by a suitably preprogrammed address selector 33 using the system clock pulses for input timing.

Once derived from the RAM 32, in the correct sequence, the processing is substantially that of the method of U.S. Pat. No. 4,070,611 to achieve two dimensional Fourier Transform in circuits 34, the transformed signals, now the matrix values for the final representation, being entered in another RAM store 35.

If desired, instead of the Fourier Transform circuits being two dimensional, they may provide a one dimensional transform which is a well established technique. For this purpose they will make two passes of circuits 34 being recirculated from RAM store 35 on a line 36. They will, of course, need to be reordered to be transferred in the orthogonal dimension and this is achieved by another suitably preprogrammed address selector 37.

Variations of the circuit given, for controlling the pulsed field gradients and for handling the FID signals, may readily be devised within the scope of this invention.

What we claim is:

1. A method of examining a slice of a body by nuclear magnetic resonance, the method including the steps of: applying magnetic fields to cause resonance preferentially in said slice; applying a first pulsed magnetic field having a gradient across the slice in a first direction to produce phase dispersion in said resonance in said direction in the slice, the direction of the field being periodically reversed; applying a second repetitively pulsed magnetic field having a gradient across the slice in a second direction orthogonal to the first to produce a further phase dispersion in the second direction, the direction of said second field being the same during each pulse, the timing and magnitude of these field gradients being such that the slice is effectively divided into a matrix of elements, the nuclei within each of a plurality of parallel strips orthogonal to the direction of the gradient of the first pulsed magnetic field resonating within a unique frequency band and nuclei at different positions along each strip being distinguishable by phase dispersion caused by the second pulsed magnetic field; sensing free induction decay and rephasing signals emitted by the nuclei as the field gradient pulses are applied; reversing the rephasing signals to form in effect further free induction decay signals; arranging the first and further free induction decay signals in a two dimensional array to give free induction decays in the two orthogonal directions; and subjecting the signals of the array to a two dimensional Fourier Transform process.

2. A method according to claim 1 in which a pulse of the second repetitively pulsed magnetic field occurs at and midway between each reversal of the first pulsed magnetic field.

3. A method according to any one of claims 1 or 2 in which the first pulsed magnetic field is of zero amplitude during the pulses of the second repetitively pulsed magnetic field.

4. A method according to claim 1 in which the second repetitively pulsed magnetic field comprises a plurality of series of pulses of equal magnitude, each series following a variable magnitude prepulse, and wherein the spins of the nuclei are rephased between each said series.

5. A method according to claim 4 in which the first prepulse is of zero amplitude and the prepulses of the succeeding series are each of greater magnitude than the preceding one.

6. A method according to claim 5 in which the prepulses increase in magnitude in equal increments.

7. A method according to claims 4 in which there are n series of pulses and the prepulses increase in magnitude by a factor of $(1/n) \times$ the magnitude of the pulses of the series.

8. A method according to claim 7 in which the amplitude of the pulses of the first pulsed field are reduced and the duration increased each by a factor of n.

9. A method according to claim 7 in which $n=5$.

10. A method according to claim 4 in which the FID and reversed rephasing signals measured for all of said sequences are interlaced to form said array in order of increasing field integral of the second pulsed magnetic field for which they were measured.

11. A method according to claim 4 in which each rephasing is by applying magnetic fields opposing the total magnetic fields applied since the preceding rephasing.

12. A method of examining a slice of the body of a patient by means of nuclear magnetic resonance, the method including: applying magnetic fields to cause resonance preferentially in nuclei in said slice; applying a first further magnetic field having a gradient in a first direction in the slice, the direction of the gradient being periodically reversed, to produce phase dispersion in said resonance in said direction in the slice; sensing a free induction decay signal emitted by the nuclei after the initial application of the first further magnetic field and rephasing the free induction decay signals emitted after each reversal thereof; applying a second further magnetic field having a gradient in a second direction in the slice, substantially orthogonal to the first direction, to produce further phase dispersion in the second direction, the second further magnetic field being repetitively pulsed to render the phase dispersion in the second direction discontinuous and the direction of said second further magnetic field being the same during each pulse; reversing the rephasing signals to form in effect further free induction decay signals; arranging the first and further free induction decay signals in a two dimensional array to provide effective free induction decays in the two orthogonal directions in the slice; and subjecting the signals of the array to a two dimensional Fourier transformation to provide distinguishable signals for individual elements of a two dimensional array of elemental areas of the slice.

13. A method according to claim 12 in which a pulse of the second further magnetic field occurs between each free induction decay or rephasing signal.

14. A method according to any one of claims 12 or 13 in which the pulses of the second further magnetic fields are divided into n sets of pulses, each set having a variable magnitude prepulse and a plurality of equal magnitude pulses, the first prepulse being of zero magnitude and subsequent prepulses exceeding the magnitude of the preceding one by $(1/n) \times$ the magnitude of the constant magnitude pulses.

15. A method of examining a slice of the body of a patient by nuclear magnetic resonance, the method including: applying magnetic fields to cause resonance preferentially in said slice; applying a first magnetic field having a gradient across the slice in a first direction to produce phase dispersion in said resonance in said direction in the slice, applying a second magnetic field having a gradient across the slice in a second direction, substantially orthogonal to the first, to produce a further phase dispersion in the second direction, and being repetitively pulsed during the application of the first magnetic field, the direction of the second field being the same during each pulse, the magnitudes of the first and second magnetic fields and the timing of the reversal of the first magnetic field and the pulse repetition rate of the first and second magnetic fields respectively being chosen so as to effectively divide the slice into a two dimensional matrix of elements, a characteristic of each element being distinguishable on the basis of resonance signals emitted thereby.

16. An apparatus for examining the body of a patient by means of nuclear magnetic resonance, the apparatus including: means for preferentially causing resonance of nuclei in a substantially planar slice of the patient; means for applying to the patient a magnetic field having a gradient across the slice in a first direction to produce phase dispersion in said resonance in said first direction, the direction of said gradient being periodically reversed; means for applying to the patient a further magnetic field having a gradient across the slice in a second direction substantially orthogonal to the first to produce a further phase dispersion in the second direction, the further magnetic field being repetitively pulsed during the application of the first mentioned magnetic field, the direction of said further magnetic field being the same during each pulse; means for detecting resonance signals from said nuclei during application of the magnetic field and the further magnetic field; and means for subjecting the resonance signals to two dimensional Fourier transformation to provide information representing a two dimensional matrix of elements in said slice for display.

17. An apparatus according to claim 16 in which the means for applying the further magnetic field is arranged to provide a pulse thereof at and midway between each reversal of the first mentioned magnetic field.

18. An apparatus according to claim 16 in which the detecting means detect free induction decay signals and rephasing signals, and means are provided for reversing the rephasing signals to produce in effect further free induction decay signals prior to said Fourier transformation.

19. An apparatus according to any one of claims 16, 17 or 18 in which the means for applying the further magnetic field is arranged to provide it as a plurality of series of pulses of constant magnitude, each with a prepulse of variable magnitude, the magnitude of the prepulse increasing with succeeding series.

* * * * *